United States Patent
Chaibi et al.

(10) Patent No.: US 10,591,494 B2
(45) Date of Patent: Mar. 17, 2020

(54) IN VITRO DIAGNOSIS DEVICE AND USES THEREOF

(71) Applicant: Abo Diag, Martillac (FR)

(72) Inventors: Najim Chaibi, Villenave d'Ornon (FR); Sylvain Malgouries, Gradignan (FR); Megumi Lucas, Martillac (FR)

(73) Assignee: Diagast, Loos (FR)

( * ) Notice: Subject to any disclaimer, the term of this patent is extended or adjusted under 35 U.S.C. 154(b) by 588 days.

(21) Appl. No.: 14/406,539

(22) PCT Filed: Jun. 11, 2013

(86) PCT No.: PCT/FR2013/051358
§ 371 (c)(1),
(2) Date: Dec. 9, 2014

(87) PCT Pub. No.: WO2013/186482
PCT Pub. Date: Dec. 19, 2013

(65) Prior Publication Data
US 2015/0140579 A1  May 21, 2015

(30) Foreign Application Priority Data
Jun. 11, 2012 (FR) .................... 12 55452

(51) Int. Cl.
| G01N 33/53 | (2006.01) |
|---|---|
| G01N 33/80 | (2006.01) |
| B01L 3/00 | (2006.01) |
| G01N 33/52 | (2006.01) |
| G01N 33/543 | (2006.01) |
| G01N 33/68 | (2006.01) |

(52) U.S. Cl.
CPC ............ *G01N 33/80* (2013.01); *B01L 3/5023* (2013.01); *B01L 3/5085* (2013.01); *G01N 33/525* (2013.01); *G01N 33/54386* (2013.01); *G01N 33/54393* (2013.01); *G01N 33/6854* (2013.01); *B01L 2300/069* (2013.01); *B01L 2300/0663* (2013.01); *B01L 2300/0829* (2013.01); *B01L 2300/161* (2013.01); *G01N 2800/22* (2013.01); *Y10T 29/49826* (2015.01)

(58) Field of Classification Search
CPC .. G01N 33/80; G01N 33/525; G01N 33/6854; G01N 33/54393; G01N 33/54386; G01N 2800/22; B01L 3/5085; B01L 3/5023; B01L 2300/0829; B01L 2300/069; B01L 2300/0663; B01L 2300/161; Y10T 29/49826
See application file for complete search history.

(56) References Cited

U.S. PATENT DOCUMENTS

| 4,797,259 | A | * | 1/1989 | Matkovich | ............. | B01D 61/18 |
|---|---|---|---|---|---|---|
| | | | | | | 356/246 |
| 4,902,481 | A | * | 2/1990 | Clark | ..................... | B01D 61/18 |
| | | | | | | 210/335 |
| 5,185,127 | A | | 2/1993 | Vonk | | |
| 2005/0124077 | A1 | | 6/2005 | Cole et al. | | |
| 2008/0261248 | A1 | | 10/2008 | Lalezari | | |
| 2008/0318342 | A1 | | 12/2008 | Durack et al. | | |
| 2010/0184102 | A1 | * | 7/2010 | Chaibi | ................... | G01N 33/80 |
| | | | | | | 435/7.25 |

FOREIGN PATENT DOCUMENTS

| CA | 1312265 | C | | 1/1993 | | |
|---|---|---|---|---|---|---|
| EP | 0334015 | A2 | | 9/1989 | | |
| EP | 0367468 | A1 | | 5/1990 | | |
| EP | 0408378 | A2 | | 1/1991 | | |
| EP | 2167967 | A2 | | 3/2010 | | |
| EP | 2315024 | A1 | | 4/2011 | | |
| FR | 2892820 | A1 | | 5/2007 | | |
| FR | 2917174 | A1 | | 12/2008 | | |
| JP | S61-152700 | A | | 7/1986 | | |
| KR | 10-2006-0126964 | A | | 12/2006 | | |
| KR | 10-2011-0017387 | A | | 2/2011 | | |
| RU | 2398235 | C2 | | 8/2010 | | |
| WO | 98/20348 | A1 | | 5/1998 | | |
| WO | 98/25758 | A1 | | 6/1998 | | |
| WO | 02052263 | A1 | | 7/2002 | | |
| WO | WO02052263 | | * | 7/2002 | ............. | G01N 33/52 |
| WO | 03/008933 | A2 | | 1/2003 | | |
| WO | 03016902 | A1 | | 2/2003 | | |

(Continued)

OTHER PUBLICATIONS

PBS-Tween 20 (PSBT) Recipe retrieved from (http://www.openwetware.org/wiki/PBST on Mar. 2, 2017).*

(Continued)

*Primary Examiner* — Julie Wu
*Assistant Examiner* — Carmencita M Belei
(74) *Attorney, Agent, or Firm* — Banner & Witcoff, Ltd.

(57) ABSTRACT

The invention relates to an in vitro diagnosis device (10) for the detection of at least one reaction between an erythrocytic phenotype antigen and an antibody specifically directed against said antigen in a sample of blood or one of the components thereof. The device is characterized in that it comprises: a substrate (12); and a hydrophobic porous membrane (14) having a thickness of between 0.5 mm and 1.5 mm and a pore diameter of between 2 and 30 μm, said membrane comprising at least one hydrophilic reaction zone (16) intended to receive the sample. The invention also relates to the uses of said device in immunohematology.

12 Claims, 1 Drawing Sheet

(56) References Cited

FOREIGN PATENT DOCUMENTS

Figure 1:
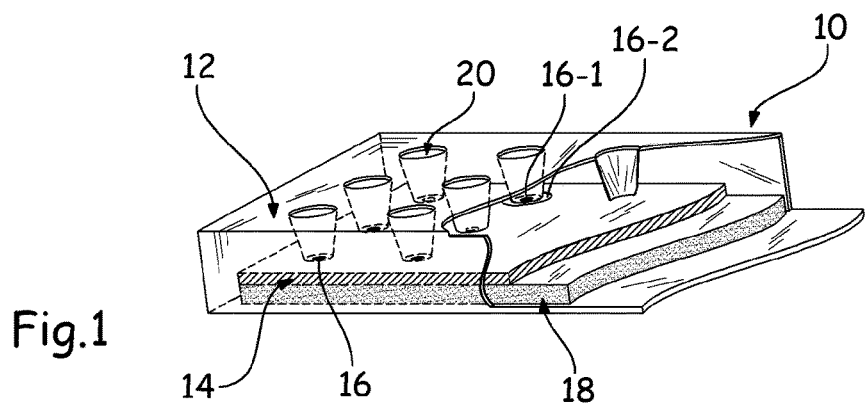

| WO | 2005057214 A1 | 6/2005 |
| WO | 2007025558 A1 | 3/2007 |
| WO | 2007/064462 A1 | 6/2007 |
| WO | 2008/049083 A2 | 4/2008 |
| WO | 2010/056889 A2 | 5/2010 |
| WO | 2012/010666 A1 | 1/2012 |

OTHER PUBLICATIONS

Sep. 17, 2013 (WO) International Search Report—App PCT/FR2013/051358.

* cited by examiner

IN VITRO DIAGNOSIS DEVICE AND USES THEREOF

The present invention relates to an in-vitro diagnosis device, from a sample of blood or one of its components, for detecting reactions between erythrocytic antigens and antibodies directed specifically against these antigens.

The invention also applies to uses of this device for identification and determination of blood groups.

The aim of immuno-haematological diagnoses is to provide or diagnose an attack of red blood cells by antibodies. For this, it is necessary to have tools for determining antigens present at the surface of the red blood cells, their presence or their absence defining the blood group, but also to identify whether blood contains one or more antibodies directed against the known antigens of red blood cells, the presence of an antibody meaning the possibility of incompatibility.

Customary techniques therefore consist of searching for and identifying the presence or absence of blood group antigens at the surface of erythrocytes and/or searching for and identifying the presence or the absence of anti-antigen antibodies of blood group in the plasma.

For example, for the ABO system, the Beth-Vincent test determines antigens carried by the red blood cells, and the complementary Simonin-Michon test or serum crosscheck determines antibodies circulating in the serum.

In the Beth-Vincent test, the red blood cells of the individual are brought together with reagents of antibodies of known specificity. Generally, this test is made visible by observation of agglutination of red blood cells when the antibodies recognise the corresponding erythrocytic antigens.

In the Simonin test, the plasma of the individual is brought together with red blood cell tests each belonging to a precise antigenic group of the ABO system. This is a test of agglutination of red blood cell tests with the plasma of the individual.

Searching for so-called irregular antibodies entails detecting the presence or absence in the blood of an individual of immunoglobulins directed against various erythrocytic antigens. In the case of autoantibody research, the antibodies already fixed in vivo are searched for directly in the individual in the direct test. In the case of alloantibody search, the aim is to reveal the fixing of these immunoglobulins on red blood cell tests whereof the antigens are known, with the indirect Coombs' technique.

There is a large number of processes and devices used for phenotyping in the field of immuno-haematology, but existing phenotyping techniques of blood groups have many disadvantages.

Microplating techniques for example need a centrifuging phase followed by an agitation step. The agitation step is critical since multiples reactions simultaneously present on the support do not have the same resuspension kinetics. There is therefore the risk of undoing weak agglutinations without succeeding in resuspending strong agglutinations. They must be carried out under visual check and particular attention must be paid to adherence phenomena of some reagents.

Similarly, while filtration techniques by gel test are being conducted, there is also the risk of not detecting some agglutinations especially during the plasmatic Reverse test of the ABO group due to dissociation by shearing of small agglutinates as they pass into the gel.

Also, there is a major disadvantage to all these techniques because they need centrifuging step to decant the red blood cells or have them pass through the gel, a restricting step which adds considerable time and the analysis costs and which needs the use of bulky centrifuges which are difficult to handle.

The method immunofiltration is also known, such as described for example in application EP-2.167.967, consisting of capturing an analyte present in a sample as it passes through a porous membrane carrying a capturing element and revealing its presence by a revelation element. This type of device comprises a deposit area of the sample, a hydrophilic porous membrane on which is deposited a capture reagent and underneath which an absorbent membrane is arranged. Conducting this type of test consists of depositing a pure or diluted sample in the sample deposit area, which passes through the porous membrane to finish in the absorbent membrane. During this travel via capillarity into the porous membrane, if the analyte corresponding to the capturing element is present in the sample, the latter is immobilised by the capture agent. In addition, it is necessary to reveal the presence on the capture spot of the preferred analyte by means of a revelation agent capable of detecting the presence of the analyte on the capture area and which bears an element letting it be detected visually (coloured product) or revealed by a physical or chemical method.

However this method has significant sensitivity and specificity problems, because when the sample is deposited it spreads and imbibes the porous membrane, and many analytes are lost in the dead volume of the porous membrane or pass outside the capture area. The same applies for the revelation solution. It is therefore necessary to oversize the absorption system to be able to deposit larger volumes of samples to be tested and revelation solution, preventing miniaturisable tests from being performed, the kinetics of which are controlled, exempt from receiving revelation agents and utilisable with an automated pipetting.

In an attempt to resolve this problem and concentrate the signal, it has been proposed in application CA1312265 or WO02052263 to interpose above and below the hydrophilic porous membrane a hydrophobic structure pierced to force the flow to pass through the capture spot. However, with these devices there is still the problem of centrifugal diffusion from a spot, and the revelation elements which pass through the capture spot and which are not fixed to it will be able to diffuse centrifugally in the hydrophilic porous membrane and be stored at the periphery of the spot. The revelation elements will then escape rinsing which is also focused on the spot. There is a return phenomenon of this revelation element in the form of a return by centripetal diffusion towards the spot, causing recolouration of the spot even in the case of absence of the preferred analyte. This phenomenon very rapidly prevents reading of the test (generally between 5 and 15 minutes) since false positive results appear. This is highly problematic since these devices do not later reinterpret the device in case of doubt, human error or loss of information.

Another major problem of existing immunofiltration devices today is control of the motion speed and in some cases pre-incubation time. These times are important since interaction between the capturing element and the analyte as well as between the analyte and the revelation element has specific kinetics. These kinetics describe the number of interactions carried out as a function of time. So as a function of capture agent/analyte couples and revelation/analyte agent, a sufficient number of interactions for each of the couples to obtain an adequate signal must be ensured. In the event where the interaction agent/analyte capture is slower, the speed of the passage of the sample across the membrane has to be regulated as a consequence. In the event where it is the interaction between the revelation element and the analyte which is limiting, it is necessary to proceed with a pre-incubation time where the revelation element and the analyte are mixing above the capture spot. Without a particular system, passing through a hydrophilic membrane is rapid (500 µl/min).

To control the flow, it has been proposed to utilise a piston, in particular in application US2008318342.

To control pre-incubation time, it has been proposed in application WO03016902 to use a device in two parts: an upper part comprising a sample collection area and a porous membrane, and a lower part comprising a porous membrane and an absorbent membrane. In the initial position these two blocks do not communicate, as fluid cannot transit via capillarity. After mechanical handling, the two areas are in contact and fluid can flow via capillarity. It has also been proposed to deposit the capturing element on a hydrophobic membrane and activate passage by addition of a surfactant.

Mechanical approaches are difficult to execute using automation since they need development and use of dedicated systems. They also expose professionals to any projections during handling.

The addition of a surfactant when the test is conducted to prime the system is very harmful as it interferes considerably in capturing agents/analytes interactions. Also, in the specific case of immunohaematology, the red blood cells used as revelation agent are not compatible with the surfactants in the form of liquid since the membrane of red blood cells is dissolved and they empty out their haemoglobin.

Another method, described in EP0334015, consists of using an extra membrane subjacent to the first to control flow, but the proposed device fails to resolve the problems linked to diffusion of the sample and the revelation element in the hydrophilic porous membrane.

Existing immuno-haematological diagnosis tests therefore have many disadvantages.

Also, the present invention aims to rectify the disadvantages of the prior art by proposing a device adapted for in-vitro immuno-haematological diagnosis by capillarity which is reliable, rapid, mobile and economical, simple to make and use, can be miniaturised and automated and has substantial sensitivity.

To respond to this aim, the present invention proposes an in-vitro diagnosis device for detection, from a sample of blood or one of its components, of at least one reaction between an antigen erythrocytic of phenotype and an antibody directed specifically against this antigen, characterized in that it comprises:
  a support, and
  a hydrophobic porous membrane of thickness between 0.05 mm and 1.5 mm and whereof the diameter of the pores is between 2 and 30 µm, said membrane comprising at least one hydrophilic reactional area intended to receive said sample, said reactional area having a surface less than the surface of the hydrophobic porous membrane.

The invention also relates to use of this device, in particular processes for phenotyping erythrocytic blood groups and detection of antibodies, executing this device.

Advantageously the present invention remedies all disadvantages arising from existing immunofiltration tests today, in particular by:
  preventing returns of revelation agent responsible for false positives
  heightened sensitivity from using lower volumes
  miniaturisation and automation of the system
  control of the kinetics of reactions without need for mechanical handling of the device.

Figure 2A:
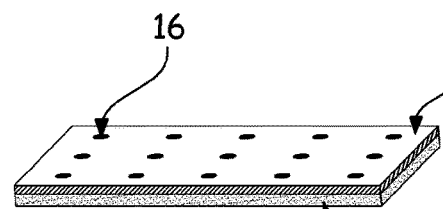
Figure 2B:
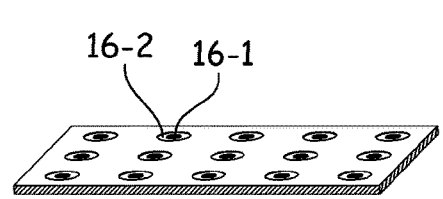
Figure 3A:
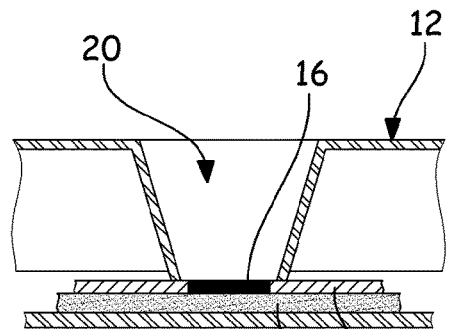
Figure 3B:
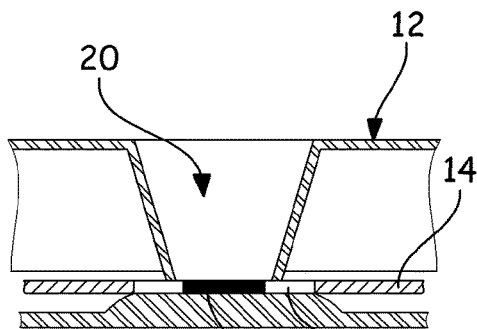
Figure 4A:
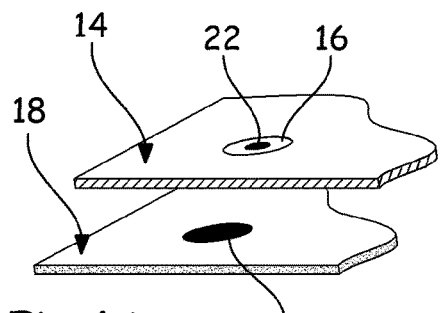
Figure 4B:
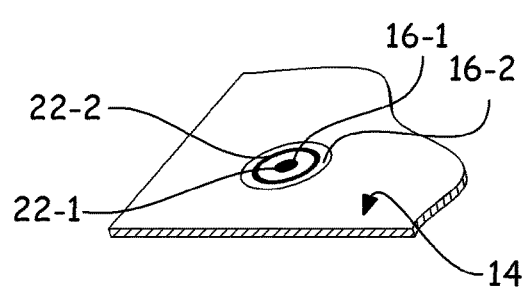

Other characteristics and advantages will emerge from the following description of the invention, given by way of example only with respect to the appended drawings, in which:

FIG. 1 illustrates a diagram of a particular embodiment of the device according to the invention viewed in perspective, FIG. 2A illustrates the hydrophobic porous membrane and the absorbent membrane of the device according to the invention with a first variant of the hydrophilic reactional areas, FIG. 2B illustrates the hydrophobic porous membrane of the device according to the invention with a second variant of the hydrophilic reactional areas, FIG. 3A illustrates a diagram of a section of the device according to the invention with a hydrophobic porous membrane corresponding to the variant shown in FIG. 2A, FIG. 3B illustrates a diagram of a section of the device according to the invention with a hydrophobic porous membrane corresponding to the variant shown in FIG. 2B, FIG. 4A illustrates the results obtained after use of the device according to the invention, on a reactional area of the hydrophobic porous membrane shown in FIG. 2A and part of the subjacent absorbent membrane, and FIG. 4B illustrates the results obtained after use of the device according to the invention, on a reactional area of the hydrophobic porous membrane shown in FIG. 2B.

The device 10 according to the invention is an in-vitro diagnosis device for detection, from a sample of blood or one of its components, of at least one reaction between an antigen of erythrocytic phenotype and an antibody directed specifically against this antigen.

This is a device for in-vitro diagnosis via capillarity, adapted particularly for immuno-haematological diagnosis in vitro.

Antigen of erythrocytic phenotype or antigen of erythrocytic group or antigen of blood group means all the immunogenic molecules present at the surface of red blood cells where needed able to cause the production of antibodies directed against it and/or allow recognition then destruction of red blood cells by the immune system.

The reaction between an antigen of erythrocytic phenotype and an antibody directed specifically against this antigen is reaction antigen-antibody called throughout the description.

Sample of blood or one of its components means the whole blood or one of its components selected especially from the red blood cell fraction, white blood cell fraction, plasma or serum.

As shown in FIG. 1, the device 10 according to the invention comprises:
  a support 12, and
  a hydrophobic porous membrane 14 comprising at least one hydrophilic reactional area 16 intended to receive the sample to be tested.

The porous membrane 14 has a thickness between 0.05 mm and 1.5 mm, preferably between 0.1 and 1 mm, even more preferably between 0.4 and 0.8 mm.

The diameter of the pores is between 2 and 30 µm, preferably between 7 and 12 µm.

The hydrophobic porous membrane 14 can comprise any material which is not altered by aqueous solvents. This material can especially be selected from natural polymers modified chemically or not, such as for example nitrocellulose polymer, cellulose or from synthetic polymers such as for example polyethylene, high-density polyethylene (HDPE) or fluorinated polymers such as PVDF. This material must be initially hydrophobic where made hydrophobic by adequate treatment. These polymers can be functionalised or not with reagent groups capable of creating links with the capturing agents used later.

The hydrophobic porous membrane 14 comprises at least one hydrophilic reactional area 16. The reactional area 16 has a surface less than the surface of the hydrophobic porous membrane 14, that is, the membrane 14 cannot be fully hydrophilised.

The reactional hydrophilic area(s) 16 of the porous membrane 14 have preferably been made hydrophilic by addition of detergent locally, without modification of the chemical functions of the porous substrate by prior chemical or physical treatment of the hydrophobic porous membrane 14.

Detergent means any hydrophilising agent, that is, any substance capable of making hydrophobic the membrane 14 hydrophilic.

The detergent used can be selected from natural detergents, natural detergents modified chemically or obtained by chemical synthesis. Preferably, this is a non-ionic surfactant, for example t-octylphenoxypolyethoxyethanol sold under the trademark Triton X-100, polysorbate 20 sold under the trademark Tween 20 or saponin.

The detergent can be diluted in an aqueous solution or an organic solvent such as ethanol, at a concentration between 0.01 and 5%. Preferably, the detergent used to make the membrane 14 hydrophilic locally is used at a dose between 0.01 and 2% (weight/volume).

The quantity of detergent used, correlated to the other characteristics of the membrane (porosity and thickness in particular) controls the motion speed of fluids which pass through the membrane. It is generally admitted that a maximal dose of 0.1% for the TritonX-100 and 0.05% for the Tween does not need to be exceeded to make a membrane intended to receive a capturing element hydrophilic. But because of the particular characteristics of the membrane 14 according to the invention, detergents capable of making this membrane hydrophilic locally can be used up to 2%, especially for Triton X-100 or Tween-20, without disrupting the reactivity of the area, which makes hydrophilisation of the membrane 14 easier.

A same hydrophobic membrane 14 can comprise several hydrophilic reactional areas 16, on condition that these areas do not intersect.

The reactional areas 16 can be in all geometric forms, but preferably in the form of circles or spots of diameter between 0.3 mm and 20 mm.

The reactional area 16 can be hydrophilic over the entire thickness of the porous membrane 14 and/or at the surface.

The reactional area 16 can have a single degree of hydrophilisation as shown in FIGS. 2A, 3A and 4A. This configuration is particularly adapted to detection of the specific presence of antibodies in the sample to be analysed.

According to a variant, the reactional area 16 can comprise several areas having different degrees of hydrophilisation.

As shown in FIGS. 2B, 3B and 4B, the reactional area 16 can comprise two hydrophilic areas 16-1, 16-2 with a greater degree of hydrophilisation at the centre 16-1 of the reactional area than at the periphery 16-2. These hydrophilic areas are preferably only at the surface of the membrane 14.

The reactional area 16 can also comprise two hydrophilic areas with a different degree of hydrophilisation, one at the surface, and the other in the thickness.

In the case where a reactional area 16 comprises two hydrophilic areas, the reactional area 16 has been made hydrophilic with two different detergents without modification of chemical functions of the porous substrate by prior chemical or physical treatment of the porous membrane.

Advantageously, the configuration of the reactional area 16 with two regions having different hydrophilisation, in particular at the surface, such as shown in FIGS. 2B, 3B and 4B, responds to a particular preoccupation of transfusion professionals, specifically to distinguish any coexistence of two populations, one being positive and the other negative, a phenomenon called mixed field population. This configuration is particularly adapted to detection and identification of particular antigens in the sample to be tested.

The hydrophilic reactional area 16 of the porous membrane 14 can comprise capturing agents. The capturing agents are absorbed or linked covalently to the membrane 14.

Capturing agents mean any chemical or biological element fixed on the area 16 capable of holding the relevant analyte contained in the sample to be tested, alone or complexed with a revelation agent.

When the aim is to identify the presence of particular antibodies in the sample to be tested, these capturing agents comprise antigens of particular erythrocytic phenotype. They can be antigens purified or not, of fragments or membranes of cells carrying antigens, void cells or not carrying the antigens or even recombinant proteins or antigens obtained by synthesis. Preferably, the capturing agents are red blood cells void of haemoglobin, carrying the antigens.

When the aim is to identify the presence of particular antigens in the sample to be tested, the capturing agents are antibodies.

The capturing agents, when present on the reactional area 16, can be deposited at the same time as the detergent serving to hydrophilise the membrane 14 to delimit the reactional area 16, or after hydrophilisation, independently of the detergent.

The capturing agents can be deposited on the reactional area 16 in a non-denaturing buffer comprising a pH solution stabilised between pH 4 and pH 10, preferably between pH 6.5 and pH 7.8, even more preferably between pH 7 and pH 7.5. The capturing agents can be either absorbed or be linked covalently.

The capturing agents can be added to adjuvants intended to maintain their microbiological stability such as sodium azide, antibiotics and its conformational stability such as sugars (sucrose, dextrose, trehalose), as well as any other agent known to those skilled in the art to perform these functions.

The capturing agents can be present over the entire area 16 or on a part only.

The detergent and/or the capturing agents are preferably in the form of solutions which can be deposited by means of automated or manual pipettes. Advantageously, these solutions can also easily be deposited using needles which hold the preferred volume by capillarity. These needles can be made of all materials, but more particularly metallic, and have or not have a hydrophobic coating. Their ends can be flat or have a notch of determined volume.

The depositing of detergent and/or capturing agents solutions must be followed by drying of the membrane, the period of drying depending on the temperature applied: at least 4 hours at room temperature, at least one hour at 37° C.

The device according to the invention can comprise an absorbent membrane 18 under the porous membrane 14. This membrane 18 absorbs liquids deposited at the level of the reactional areas 16, which are not retained by the membrane 14, in particular when the reactional area 16 is hydrophilic over the entire thickness of the membrane 14.

The membrane 18 can comprise material enabling passive absorption by capillarity such as absorbent paper, cellulose, etc., or made of absorbent polymers. By way of example, the following products can be cited:
- porous membrane filters, sold under the trademark Merk-Millipore® C048, C068, C083, C248 (Merk)
- filter paper, sold under the trademark Whatman® CF3, CF4, CF10, Grade 470, CF5, CF6, CF7, Grade 900, Grade 300
- fiber-based material, sold under the trademark Ahlstrom® Grades 601, 642, 631, 238, 237, 222, 243, 320 (Munktell)
- Pall Grades 111, 113, 133, 165, 197, 8975, 8964, 8301 (Pall Corporation), microporous polymeric sheets, sold under the trademark Accuwik® Ultra
- super absorbent material, sold under the trademark Cleanis Gelmax® superabsorbent pad
- Cotton The composition of the absorbent membrane 18 and its dimensions must be selected so they can absorb all the solutions used during the test ($V_{total}$ in µl). Each membrane being characterized by an absorption capacity (C in µl/cm$^2$), the membrane and its dimensions (D in cm$^2$) are selected to satisfy the following equation: $D > V_{total}/C$.

Alternatively, the liquid can be absorbed by a pressure differential between the area above the membrane and the area below it. For example using an aspiration system with partial vacuum.

The membrane 14 and optionally the membrane 18, are arranged in a support 12.

The support 12 of the device 10 according to the invention is preferably a rigid support. It can be for example a shell.

The support preferably comprises rigid material not letting liquid escape. This can be in particular plastic materials such as polypropylene, polyethylene, polystyrene, acrylonitrile butadiene styrene, polyethylene terephthalate, polycarbonate, polyamide, polyvinyl chloride, methyl poly-methacrylate.

The support 12 preferably comprises at least one opening 20, each opening 20 being at right angle of each hydrophilic reactional area 16 of the porous membrane 14. This opening 20 corresponds to the collection area of the sample deposited on the hydrophilic reactional area 16. The hydrophilic area 16 can be of a size identical to that of the base of the opening, smaller or larger, provided two hydrophilic areas are always separated by a hydrophobic area on the membrane 14.

The openings 20 can have transparent edges for viewing the subjcent signals, if needed.

The collection area must be of a size such that it can contain at least the maximum volume of sample to be tested deposited on the reactional membrane 16.

The independence of each reactional area 16 is obtained by the barrier comprised by the hydrophobic membrane between the reactional areas. This independence performs several different diagnoses on the same device comprising a single membrane. According to a variant, this independence can also optionally be embodied by segmenting the support 12 into physically independent units separated by partitions each containing its own membrane.

In addition, it is possible to improve contact between the membranes 14 and 18 by creating excessive thickness around the opening 20, and at the bottom of the opening a dome opposite the opening of said opening 20.

The support 12 can be a shell having several openings 20, of dimensions compatible with the standard SBS/AINSI in its external dimensions.

The device 10 according to the invention can be used to determine the presence or absence of an analyte in a biological fluid, in particular in the blood or one of its constituents by capillarity. This analyte can be an antigen of blood phenotype or an antibody directed against this antigen.

The device 10 can be utilises especially for:
- phenotyping red blood cells, that is, determination of antigens at their surface.
- Simonin test which identifies the presence of anti-A or anti-B antibodies.
- search for or identification of antibodies directed against antigens in particular erythrocytic in terms of the search for alloantibodies, autoantibodies or even cold agglutinins.

Specifically, the aim of the invention therefore is the use of a device 10 for identifying and determining ABO blood groups, extended Rhesus phenotyping, search for irregular agglutinin, search for autoantibodies, search for cold antiglobulin and/or cross validation, from a sample of blood or one of its components.

Use of the device 10 according to the invention requires use of a revelation agent. Preferably they are red blood cells. These red blood cells:
- are red blood cells of known phenotype, called red blood cell tests, for use of the device to search for antibodies or the Simonin test,
- are those contained in the sample to be tested for use of the device for phenotyping.

As a function of the analyte whereof the aim is to detect the presence in the sample to be tested, the nature of the capture agent, the nature of the revelation agent, the hydrophilisation method (simple or multiple, in thickness or surface) and the follow-up protocol all need to be varied.

In all cases, prior to deposit of the sample to be tested on the reactive area, it is possible to proceed with hydration of the reactional area 16 by means of a buffer solution. This buffer can comprise a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (Tween 20 from 0.01 to 0.05% m/v), saturation agents (BSA) and/or agents capable of potentialising antigen-antibody reactions.

Similarly, to read the results it is necessary to use a buffer rinsing. This washing buffer preferably comprises PBS, TBS or saline solution of pH between 2 and 10, preferably between 5 and 9. The osmolarity of the buffer must be controlled to avoid haemolysis of red blood cells. The buffer must be selected so as not to detach the revelation agents or the coloured analytes fixed directly or indirectly to the capturing agents. Surprisingly, for use of the device according to the invention it is preferable to use lightly hyperosmotic washing solutions (that is, between 300 mOsm and 800 mOsm) obtained by the presence of saline agents such as NaCl or non-ionic osmolites such as for example glycine or taurine. This buffer can be coloured with colours contrasting with the colour of the revelation agent. For example if the revelation agents are red blood cells, the washing buffer solution can be coloured blue or green. It is also possible to add a low dose of surfactant to the washing solution to eliminate background noise. These surfactants are preferably non-ionic surfactants, and in particular esters of sugar, especially polyoxyethylenic esters of sorbitan (Tween).

During use of the device 10, liquids can be deposited especially by means of a pipetter system or by means of a capillarity replication system.

Advantageously, the device according to the invention needs neither centrifuging, nor agitation, nor vacuuming, nor ad hoc device. It can also be used manually totally autonomously, and easily be automated. The different characteristics of the membrane 14 control the motion speed and produce motion times long enough to enable antigen-antibody reaction, in spite of the porosity sizes of the membrane 14, however large.

According to a first variant, the aim of the invention is the use of the device 10 for phenotyping red blood cells.

The aim is to search for antigens at the surface of red blood cells. In this case, an antibody or a mixture of antibodies is used as capturing agent, capable of recognising specifically the antigen in question or a variant of an antigen. The antibodies can be a purified or semi-purified monoclonal antibody, a culture surfactant containing the monoclonal antibody (see Table 1) or a polyclonal antibody, an antiserum. Agglutinins or lectins can also be used.

A non-exhaustive list of monoclonal antibodies follows:

TABLE 1 non-exhaustive list of antibodies of captures utilisable for globular phenotyping

| Preferred antigen | Capturing Element | Example of reference clones | revelation Element |
|---|---|---|---|
| A | Ac Anti-A | BIRMA-1, | Red blood cells of the sample |
| B | Ac Anti-B | LB-2 and/or ES-4 | Red blood cells of the sample |
| AB | Ac Anti-AB | ES-4 and/or ES-15 and/or BH517 | Red blood cells of the sample |
| D (RH1) | Ac Anti-D | RUM-1 and/or MS-201 and/or MAD-2 and/or TH-28 and/or MS-26 | Red blood cells of the sample |
| C (RH2) | Ac Anti-C | MS-273 or MS-24 | Red blood cells of the sample |
| c (RH4) | Ac Anti-c | MS-33 | Red blood cells of the sample |
| E (RH3) | Ac Anti-E | MS-258, MS-80 | Red blood cells of the sample |
| e (RH5) | Ac Anti-e | MS-16, MS-21, MS-63 | Red blood cells of the sample |
| K | Ac Anti-K | MS-56 | Red blood cells of the sample |
| Fya (FY1) | Ac Anti-Fya | P3TIM | Red blood cells of the sample |
| Fyb (FY2) | Ac Anti-Fyb | | Red blood cells of the sample |
| Jka (JK1) | Ac Anti-Jka | MS-15 | Red blood cells of the sample |
| Jkb (JK2) | Ac Anti-Jkb | MS-8 | Red blood cells of the sample |
| S (MNS3) | Ac Anti-S | MS-94 | Red blood cells of the sample |
| s (MNS4) | Ac Anti-s | P3BER L | Red blood cells of the sample |
| Lea (LE1) | Ac Anti-Lea | LM112/161 | Red blood cells of the sample |
| Leb (LE2) | Ac Anti-Leb | LM129/181 | Red blood cells of the sample |
| M (MNS1) | Ac Anti-M | M110/140 | Red blood cells of the sample |

TABLE 1-continued non-exhaustive list of antibodies of captures utilisable for globular phenotyping

| Preferred antigen | Capturing Element | Example of reference clones | revelation Element |
|---|---|---|---|
| N (MNS2) | Ac Anti-N | | Red blood cells of the sample |
| P1 | Ac Anti-P1 | P3MON23 | Red blood cells of the sample |
| Kpa (KEL3) | Ac Anti-Kpa | | Red blood cells of the sample |
| Lua (LU1) | Ac Anti-Lua | | Red blood cells of the sample |
| Lub (LU2) | Ac Anti-Lub | | Red blood cells of the sample |
| k, cellano (KEL 2) | Ac Anti-k | | Red blood cells of the sample |
| Kpb (KEL4) | Ac Anti-Kpb | | Red blood cells of the sample |
| Cw | Ac Anti-Cw | | Red blood cells of the sample |

According to a particular embodiment, the aim of the invention is a process for phenotyping erythrocytic blood groups from a sample of red blood cells (pure red blood cells or total blood) for simultaneous detection of a population of positive phenotype and a population of negative phenotype (double population), comprising the following steps:

depositing a solution to hydrate the porous membrane 14 at the centre of the reactional area of a device 10 according to the invention, said reactional area 16 comprising two hydrophilic areas 16-1, 16-2 with a degree of hydrophilisation greater at the centre 16-1 of the reactional area than at the periphery 16-2, and comprising at the centre capturing agents comprising antibodies; the solution for hydration of the membrane is a solution known to be favourable to immuno-haematological reactions containing optionally additives, such as for example a buffer comprising a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (especially Tween 20 from 0.01 to 0.05% m/v), saturation agents (for example BSA) and/or agents capable of potentialising antigen-antibody reactions. This buffer can optionally have protease activity for example obtained by the addition of enzymes such as papain or bromelain. This buffer can optionally contain polycationic agents such as polybrene or polylysin, for potentialising the reaction and keeping the blood cells in longer contact with the capturing element;

diluting the red blood cells to be phenotyped in a buffer solution, specifically a buffer solution known to be favourable to immuno-haematological reactions optionally containing additives such as for example a buffer comprising a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (especially Tween 20 from 0.01 to 0.05% m/v), saturation agents (for example BSA) and/or agents capable of potentialising antigen-antibody reactions. This buffer can optionally have protease activity for example obtained by the addition of enzymes such as papain or bromelain. This buffer can optionally contain polycationic agents such as polybrene or polylysin, for potentialising the reaction and keeping the red blood cells in longer contact with the capturing elements;

adding this solution containing the red blood cells to be phenotyped at the centre of the reactional area 16-1;

incubating, preferably at a temperature between 15 and 40° C., in particular between 18° C. and 25° C., for a period from 60 seconds to 15 min in particular from 2 min to 10 min;

depositing a rinse solution on the reactional area; the rinse solution being a solution known not to be harmful for antigen-antibody reactions, maintaining the integrity of the red blood cells and capable of undoing non-specific interactions, such as for example a buffer comprising a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (especially Tween 20 from 0.01 to 0.05% m/v), saturation agents (for example BSA) and/or agents capable of potentialising antigen-antibody reactions. In the case of prior use of polycationic agent, this buffer shall be strongly ionic, for example, it shall contain more than 100 mM of NaCl to be able to undo non-specific interactions caused by this type of additive.

The sample to be deposited can be red blood cells or of the total blood. The sample can be diluted in a buffer comprising a solution of stabilised pH between pH 6 and pH 8.5, preferably between pH 6.5 and pH 7.8, in particular between pH 7 and pH 7.5 and of osmolarite between 250 mOsm and 800 mOsm, preferably between 300 mOsm and 600 mOsm. This solution can optionally contain detergents in low concentration (especially Tween 20 from 0.01 to 0.05% m/v), saturation agents (for example BSA) and/or agents capable of potentialising antigen-antibody reactions. This buffer can optionally exhibit protease activity for example obtained by the addition of enzymes such as papain or bromelain.

Hydrophilisation of the reactional areas 16 of the membrane 14 of the device 10 used to execute this process is preferably surface hydrophilisation.

Hydrophilisation can for example be performed by means of a solution of Tween 20 in ethanol at a concentration between 0.1% m/v and 1% m/v, preferably 0.2% m/v and 1% m/v in volume between 2 µl and 40 µl and preferably between 5 µl and 20 µl at the centre of which a hydrophilisation area is created in the thickness made by means of an aqueous solution of Triton X100 of concentration between 0.1% m/v and 2% m/v, preferably 0.5% m/v and 1% m/v in volume between 25 nl and 15 µl and preferably between 100 nl and 10 µl.

If the red blood cells present in the sample possess the antigen recognised by the capturing element, the red blood cells remain immobilised at the centre of the reactional area 16 of the membrane 14 in spite of the rinsing and the central reactional area 16-1 remains red. If the red blood cells present in the sample do not carry the antigen recognised by the capturing element, the red blood cells are flushed by the rinsing: the central area 16-1 remains white and it a red ring forms in the peripheral area 16-2. If the sample contains two different populations, both a centre red 22-1 and a red peripheral ring 22-2 are observed.

Reading the results can be visual or automatic.

According to another particular embodiment, the aim of the invention is a process for typing blood groups, from a sample of red blood cells (pure red blood cells or total blood), disallowing detection of double populations, comprising the following steps:

depositing a solution to hydrate the porous membrane 14 at the centre of the reactional area of a device 10 according to the invention, said reactional area 16 comprising a single hydrophilic area and comprising capturing agents comprising antibodies; the solution for hydration of the membrane is a solution known to be favourable to immuno-haematological reactions optionally containing additives, such as for example a buffer comprising a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (especially Tween 20 from 0.01 to 0.05% m/v), saturation agents (for example BSA) and/or agents capable of potentialising antigen-antibody reactions. This buffer can optionally have protease activity for example obtained by the addition of enzymes such as papain or bromelain. This buffer can optionally contain polycationic agents such as polybrene or polylysin, for potentialising the reaction and keeping the red blood cells in longer contact with the capturing elements;

optionally diluting the red blood cells to be typed in a buffer solution, specifically a buffer solution known to be favourable to immuno-haematological reactions optionally containing additives, such as for example a buffer comprising a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (especially Tween 20 from 0.01 to 0.05% m/v), saturation agents (for example BSA) and/or agents capable of potentialising antigen-antibody reactions. This buffer can optionally have protease activity for example obtained by the addition of enzymes such as papain or bromelain. This buffer can optionally contain polycationic agents such as polybrene or polylysin, for potentialising the reaction and keeping the blood cells in longer contact with the capturing element;

adding this solution containing the red blood cells to be phenotyped at the centre of the reactional area, incubating, preferably at a temperature between 15 and 40° C. in particular between 18° C. and 25° C., for a period from 2 seconds to 15 min and in particular from 1 min to 10 min depositing a rinse solution on the reactional area the rinse solution being a known solution so as not to be harmful for antigens-antibody reactions, maintaining the integrity of the red blood cells and capable of undoing non-specific interactions, such as for example a buffer comprising a solution of stabilised pH between pH 6 and pH 8.5, preferably between pH 6.5 and pH 7.8, preferably between pH 7 and pH 7.5 and osmolarity between 250 mOsm and 800 mOsm, preferably between 300 mOsm and 600 mOsm. This solution can optionally contain detergents in low concentration (especially Tween 20 from 0.01 to 0.05% m/v), saturation agents (for example BSA) and/or agents capable of potentialising the antigen-antibody reactions. In the case of prior use of a polycationic agent, this buffer shall be strongly ionic, for example, it shall contain more than 100 mM of NaCl to be able to undo non-specific interactions caused by this type of additive.

Hydrophilisation of reactional areas 16 of the membrane 14 of the device 10 used to execute this process can be thickness hydrophilisation. It is necessary for the device 10 to also comprise an absorption system subjacent to the membrane 14, for example an absorbent membrane 18.

Hydrophilisation can be performed by means of an aqueous solution of Triton X100 of concentration between 0.1% m/v and 2% m/v, preferably 0.5% m/v and 1% w/v in volume between 25 nl and 15 µl and preferably between 100 nl and 10 µl.

If the red blood cells present in the sample carry the antigen recognised by the capturing element, the red blood cells remain immobilised at the centre 22 of the reactional area 16 of the membrane 14 in spite of the rinsing and the reactional area 16 remains red. If the red blood cells present in the sample do not carry the antigen recognised by the capturing element, the red blood cells are flushed by the rinsing and the reactional area 16 remains white. The absorbent membrane 18 absorbs (area 24) everything not fixed to the membrane 14.

Reading the results can be visual or automatic.

According to a second variant, the aim of the invention is use of the device 10 for detection of multivalent antibodies in the blood or Simonin test.

The aim is to search for specific antibodies. The capturing element therefore comprises the antigen against which the preferred antibody is directed.

The immobilised antigens can be synthetic antigens coupled or not to a polymer or to a proteic structure. These can also be recombinant proteins containing one or more sequences of the antigen or a mixture of antigen of preferred variants. The immobilised antigens can also be on cells or fragments of cells, in particular, membranous fragments or cells void of their cytoplasmic content. These cells can be in particular red blood cells void of their cytoplasm, also called «ghosts».

If the sample has antibodies directed against the antigen in question, these will remain captured at the surface of the membrane 14 at the level of the reactional area 16.

It is necessary to use a revelation element to reveal the presence of these antibodies either by recognising their antibody nature (anti-IgG, anti-IgM), or if the antibody used is multivalent (capable of detecting several antigens simultaneously) a revelation element also carrying the antigen in question can be utilised.

TABLE 2

Examples for search for antibodies in the field of the immunohaematology

| Preferred antigen | Capturing Element | Revelation Element |
| --- | --- | --- |
| IgM Anti-A | Ghosts A | Red blood cell test A1 |
| IgM Anti-B | Ghosts B | Red blood cell test B |

Another aim of the invention therefore is a process for detection of multivalent antibodies present in the blood, from a sample of plasma, serum or total blood, comprising the following steps:

depositing the sample to be tested on the reactional area 16 of a device 10, said reactional area 16 comprising capturing agents comprising antigens, adding red blood cell tests of known phenotype, comprising the same antigens as the capturing agents, letting the mixture pass through the hydrophilic area, said hydrophilic area having characteristics enabling passage time between 1 and 45 minutes, preferably between 3 and 15 minutes, depositing a rinse solution on the reactional area, such as for example a buffer comprising a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (especially Tween 20 from 0.01 to 0.05% m/v), saturation agents (for example BSA).

The sample to be deposited can be plasma, serum or whole blood diluted or not in a buffer comprising a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (for example Tween 20 0.01 to 0.05% m/v), saturation agents (especially BSA) and/or agents capable of potentialising the antigen-antibody reactions. This buffer is preferably of salinity less than 100 mM of NaCl.

Hydrophilisation of the reactional areas 16 of the membrane 14 of the device 10 used to execute this process is preferably performed in thickness. It is therefore necessary for the device 10 to also comprise an absorption system subjacent to the membrane 14, for example an absorbent membrane 18.

Hydrophilisation can be performed by means of an aqueous solution of Triton X100 of concentration between 0.3% m/v and 2% m/v, preferably 0.5% m/v and 1% w/v volume between 25 nl and 15 µl and preferably between 100 nl and 10 µl. The capturing agents can be deposited on the membrane, mixed with the detergent, or after hydrophilisation of the reactional areas 16.

If the tested plasma contains antibodies directed against the antigen present in the capture agent and in the revelation agent (red blood cell tests), a red centre 22 appears in the reactional area 16. A white centre signals the absence in the tested plasma of antibodies directed against the antigen present both in the capture agent and in the revelation agent (red blood cell tests). The absorbent membrane 18 absorbs (area 24) everything not fixed to the membrane 14.

Reading the results can be visual or automatic.

According to a third variant, the aim of the invention is the use of the device 10 to search for irregular agglutinin in the blood.

The aim is to identify the presence of red blood cells sensitised by plasmatic antibodies of the sample or by activation of the subsequent complement.

In this format, either there is no capture agent, or the latter is an aggregation agent such as a polycationic polymer.

After having incubated red blood cell panel test with the plasma, an agent capable of reversibly aggregating the red blood cells is added to the mixture. This reversible aggregation agent can be selected from polycationic polymers such as for example polybrene, polylysin or polyethyleneinmine. The red blood cells remain held and form a button of blood cells since the size of the aggregates formed is too great to let them pass through the membrane. The blood cells are rinsed of the excess of non-specific globulins by means of a solution also containing an aggregation agent to avoid destabilisation of the button. After these retained blood cells are rinsed, a multivalent Coombs' reagent is added to carry out reticulation of cells of the button if the latter are sensitised. Adding a saline buffer containing low dose of surfactant breaks the aggregates of non-sensitised cells and keeps the aggregates of reticulated sensitised cells.

TABLE 3 non-exhaustive list of antibodies utilisable in search for irregular agglutinins

| Preferred Analyte | Reticulation Agent | Clone Reference | |
|---|---|---|---|
| IgG human on red blood cell test | Anti-IgG, protein A, protein G. | MS-278, Protein A, G, A/G | red blood cell test |
| IgM human on red blood cell test | Anti-IgM | | red blood cell test |
| C3d human on red blood cell test | Anti-C3d | BRIC-8 | red blood cell test |

To execute these processes, hydrophilisation of reactional areas 16 of the membrane 14 of the device 10 used to execute this process is preferably performed in thickness. It is therefore necessary for the device 10 to also comprise an absorption system subjacent to the membrane 14, for example an absorbent membrane 18.

Hydrophilisation can be performed by means of an aqueous solution of Triton X100 of concentration between 0.3% m/v and 2% m/v, preferably 0.5% m/v and 1% w/v in volume between 25 nl and 15 µl and preferably between 100 nl and 10 µl. A reversible aggregation agent can advantageously be added, preferably selected from polycationic polymers such as for example polybrene, polylysin or polyethyleneinmine.

According to this third variant, another aim of the invention therefore is a process for detection of anti-erythrocytic antibodies present in the blood, cross validation or search for autoantibodies or cold agglutinin, from a sample of plasma, serum or total blood, characterized in that it comprises the following steps:
- to search for alloantibodies, previously incubate the sample to be tested with a buffer, red blood cell tests of known phenotype and an agent capable of aggregating the red blood cellsat a temperature between 15 and 40° C. preferably at around 37° C., for a period of between 3 and 60 minutes, preferably between 5 and 30 minutes; the buffer is a buffer of low ionic force, such as a LISS buffer (for example containing fewer than 50 mM NaCl); to search for autoantibodies, simply use the sample containing the red blood cells of the sample without previous incubation;
- adding to this mixture an agent capable of aggregating the blood cells, for example a solution of hexadimethrine bromide;
- after a period preferably between 15 seconds and 5 minutes, depositing the mixture on the reactional area 16 of a device 10 according to the invention, and letting it flow; it forms into a button of cells above the spot,
- depositing a solution containing the agent capable of aggregating the red blood cells on the reactional area, where the agent capable of aggregating the red blood cells can be for example a solution of hexadimethrine bromide, preferably with a hexadimethrine bromide concentration in the solution between 0.01 and 2% (m/v), even more preferably between 0.05 and 0.5%; this agent performs rinsing of non-specific proteins and maintains the integrity of the button of cells;
- depositing a Coombs', human antiglobulin or anti-complement reagent on the reactional area, and
- depositing a rinse solution on the reactional area such as for example a hypertonic saline solution of stabilised pH between pH 6 and pH 8.5, preferably between pH 6.5 and pH 7.8, preferably between pH 7 and pH 7.5 and osmolarity between 300 mOsm and 800 mOsm. This solution can optionally contain detergents in low concentration (for example Tween 20 0.01 to 0.05% m/v) and a dye of a colour contrasting with red (blue or green).

The sample to be deposited can be plasma, serum or whole blood diluted or not in a buffer comprising a stabilised pH solution between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (for example Tween 20 0.01 to 0.05% m/v), saturation agents (especially BSA) and/or agents capable of potentialising antigen-antibody reactions. This buffer preferably has salinity less than 50 mM in NaCl.

If the plasma tested contains antibodies directed against the antigen present in the revelation agent (red blood cell tests) or if the red blood cells of the sample are already sensitised in vivo, a red centre 22 appears in the reactional area 16. A white centre signals the absence or undetectable dose of antibodies directed against the antigen present in the revelation agent (red blood cell tests). The absorbent membrane 18 absorbs (area 24) all which is not fixed to the membrane 14.

Reading the results can be visual or automatic.

The device 10 according to the invention can be provided according to a range combining the pertinent complementary tests performed most often and simultaneously by professionals on the same card, all tests being performed and interpreted similarly.

On each of the cards, several analytes arranged in a column for several samples (donors or patients) arranged in line can be detected. This can be for example a card for:
- ABO-D blood grouping,
- Rhesus-Kell grouping,
- search for irregular agglutinin (3 erythrocytic phenotypes),
- identification of irregular agglutinins (10 erythrocytic phenotypes),
- extended phenotyping,
- direct control with antiglobulin test,
- direct compatibility test.

The device 10 according to the invention can be presented in a kit also comprising reagents necessary to execute at least one of the processes of use of said device.

The invention claimed is:

1. A device, for detection of at least one reaction between an antigen of erythrocytic phenotype and an antibody directed specifically against this antigen, from a sample of blood or one of its components, comprising:
   (i) a support, and
   (ii) a hydrophobic porous membrane, wherein the membrane has a thickness between 0.05 mm and 1.5 mm, wherein the diameter of the pores is between 2 and 30 µm, said membrane comprising at least one hydrophilic reaction area for receiving said sample, wherein a surface area of the hydrophilic reaction area is less than a surface area of the hydrophobic porous membrane, wherein the support comprises a lower part on which is deposited the porous membrane and an upper part covering the membrane, said upper part comprises at least one opening, each opening corresponding to each hydrophilic reaction area of the porous membrane, wherein the hydrophilic reaction area of the porous membrane has been made hydrophilic with a detergent without modification of the chemical functions of the porous substrate by prior chemical or physical treatment of the porous membrane prior to the deposit of either the antigen or the antibody; and wherein the detergent is a solution selected from the group consisting of between 0.01% m/v and 5% m/v polysorbate 20 in ethanol and an aqueous solution between 0.01% m/v and 5% m/v t-octylphenoxypolyethoxyethanol.

2. The device according to claim 1, wherein the support is a rigid plastic support.

3. The device according to claim 1, further comprising a capturing agent comprising the antibody or the antigen wherein the capturing agent is deposited in at least one hydrophilic reaction area of the porous membrane.

4. The device according to claim 1, wherein the antigen is of erythrocytic group/phenotype.

5. The device according to claim 1, wherein the antigen comprises red blood cells void of haemoglobin.

6. The device according to claim 1, wherein the reaction area is hydrophilic over the entire thickness of the porous membrane.

7. The device according to claim 1, wherein the reaction area comprises two hydrophilic areas with a greater degree of hydrophilisation at the center of the reaction area than at the periphery.

8. The device according to claim 1, wherein the reaction area comprises two hydrophilic areas with a different degree of hydrophilisation, one at the surface, the other in the thickness.

9. The device of claim 1, wherein the detergent is a solution selected from the group consisting of between 0.1% m/v and 5% m/v polysorbate 20 in ethanol and an aqueous solution of 0.1% m/v and 5% m/v t-octylphenoxypolyethoxyethanol.

10. A method for phenotyping erythrocytic blood groups, from a sample of red globules, comprising the following steps:

(i) depositing a solution to hydrate the porous membrane at the level of the reaction area of the device according to claim 1, said reaction area comprises a single hydrophilic area, (ii) depositing a capturing agent comprising an antibody directed specific for the red globules, (iii) optionally diluting the red globules to be phenotyped in a buffer solution, (iv) adding the solution containing the red globules to be phenotyped at the center of the reaction area, (v) incubating; and (vi) depositing a rinse solution on the reaction area.

11. A method for detection of multivalent antibodies present in the blood, from a sample of plasma, serum or total blood, comprising the following steps:

(i) depositing the sample to be tested on the reaction area of the device according to claim 1, (ii) depositing a capturing agent comprising an antigen for specific for the antibodies, (iii) adding red blood cell tests of known phenotype, comprising the same antigen as the capturing agent, (iv) having the mixture pass through the hydrophilic area; and (v) depositing a rinse solution on the reaction area.

12. A method for detection of anti-erythrocytic antibodies present in the blood, cross validation or search for autoantibodies or cold agglutinin from a sample of plasma, serum or total blood, characterized in that it comprises the following steps:

(i) incubating the sample to be tested with a buffer, red blood cell tests of known phenotype, (ii) adding to this mixture an agent capable of aggregating the red globules, (iii) depositing the mixture on the reaction area of the device according to claim 1, (iv) depositing a solution containing an agent capable of aggregating the red globules on the reaction area, (v) depositing a Coombs, human antiglobulin or anti-complement reagent on the reaction area; and (vi) depositing a rinse solution on the reaction area.

* * * * *